United States Patent [19]

Le Van Mao

[11] Patent Number: 4,732,881
[45] Date of Patent: Mar. 22, 1988

[54] CATALYSTS FOR UP-GRADING STEAM-CRACKING PRODUCTS

[75] Inventor: Raymond Le Van Mao, Montreal, Canada

[73] Assignee: The Abestos Institute, Quebec, Canada

[21] Appl. No.: 911,381

[22] Filed: Sep. 25, 1986

[51] Int. Cl.$^4$ ............................................. B01J 29/28
[52] U.S. Cl. ......................................... 502/71; 502/64
[58] Field of Search ............................. 502/60, 64, 71

[56] References Cited

U.S. PATENT DOCUMENTS 3,871,993  3/1975  Morrison ................................ 502/71
4,180,516 12/1979  Chang et al. .......................... 502/71
4,615,995 10/1986  Le Van Mao ......................... 502/71

FOREIGN PATENT DOCUMENTS 148728  8/1984  Japan ..................................... 502/60

Primary Examiner—Carl F. Dees
Attorney, Agent, or Firm—Cushman, Darby & Cushman

[57] ABSTRACT

There is provided with the present invention a new process for up-grading products resulting from the steam-cracking of hydrocarbons which comprises bringing the steam-cracking reaction products in contact with a catalyst comprising a mixture of from 2.5 to 7.5% wt of $Cr_2O_3$, 5 to 17.5% wt of $Al_2O_3$ and 75 to 85% wt of a Zn-ZSM-5 zeolite or a Zn-ZSM-5 zeolite/asbestos and recovering the desired products.

6 Claims, 3 Drawing Figures

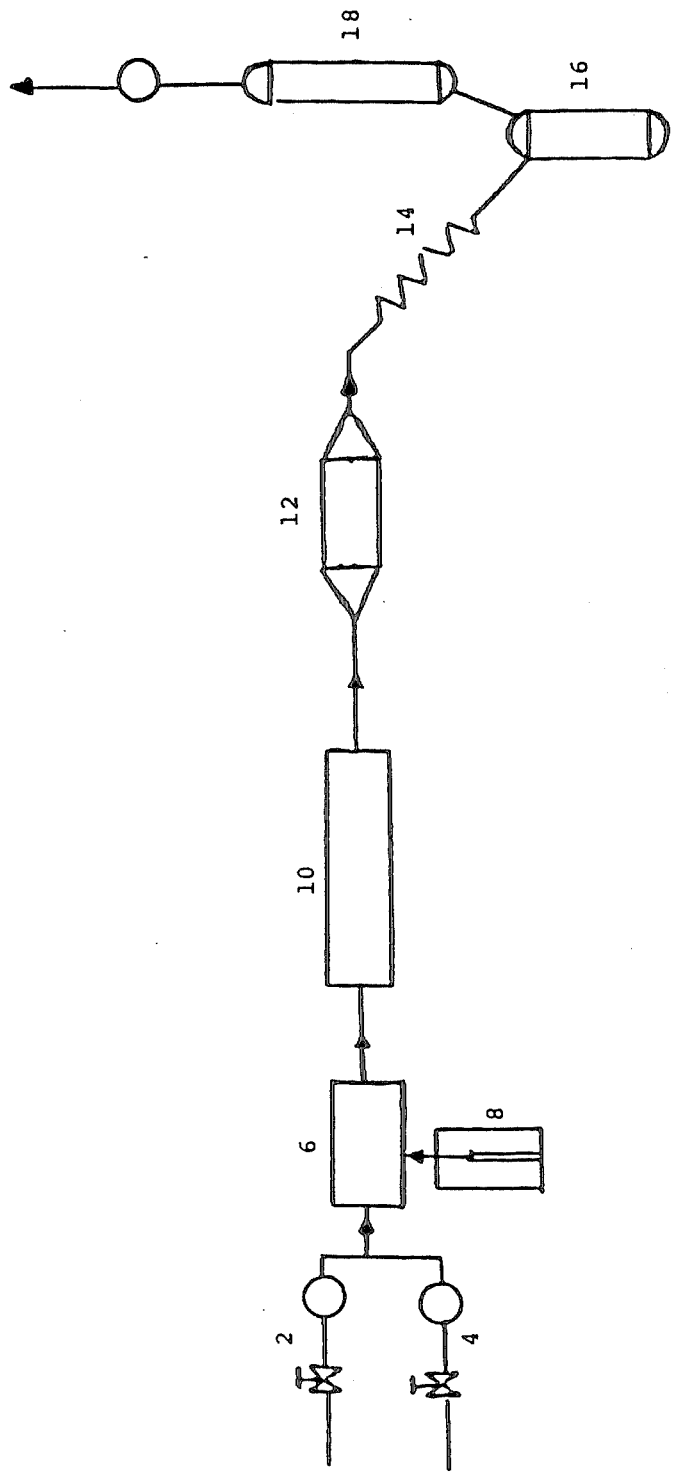
FIGURE 1: SCHEMATIC DRAWING OF THE PROCESS FOR UP-GRADING PRODUCTS RESULTING FROM THE STEAM-CRACKING OF HYDROCARBONS

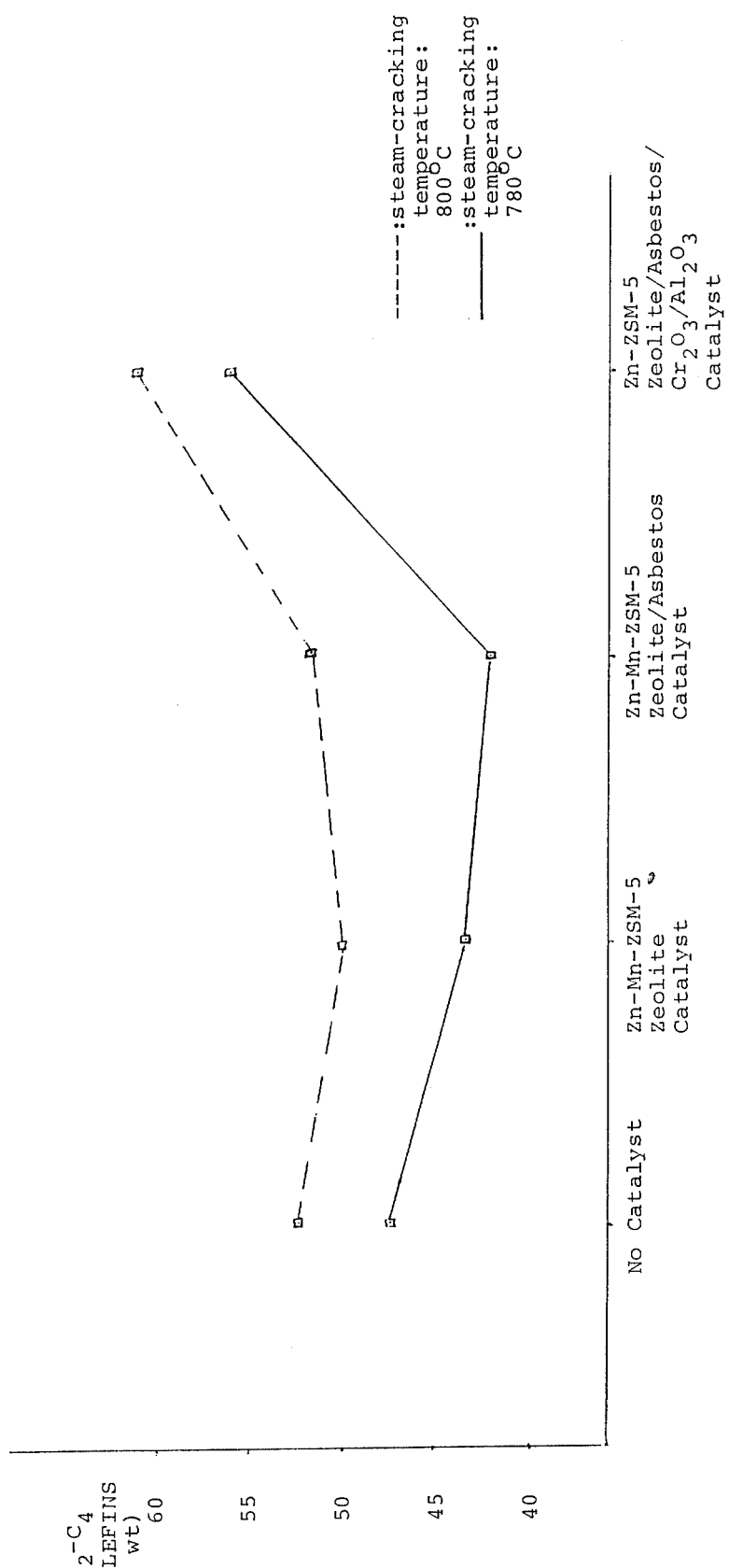

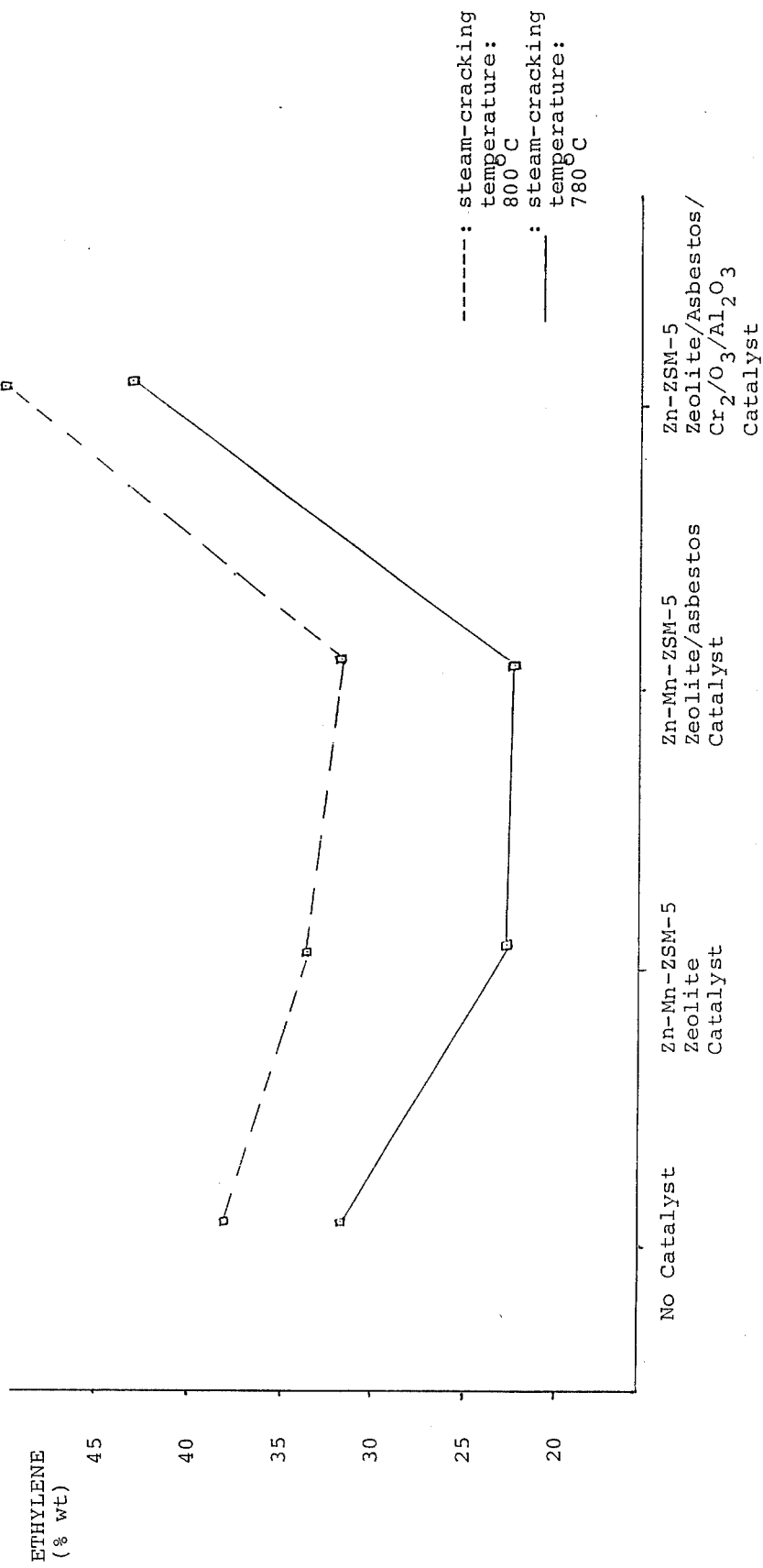

CATALYSTS FOR UP-GRADING STEAM-CRACKING PRODUCTS

BACKGROUND OF THE INVENTION

Steam-cracking is one of the most widely used basic petrochemical processes. It is used by industries to produce light olefins such as ethylene, propylene, butenes and butadiene and it is also relied upon for the production of aromatics such as benzene, toluene and xylenes.

Basically, steam-cracking comprises a step in which the hydrocarbon mixture to be transformed is mixed with steam and submitted to elevated temperatures in a tubular reactor. The different resulting products, gaseous and liquid hydrocarbons are then collected and separated. Thus, product distribution depends on the nature of the initial hydrocarbon mixture as well as experimental conditions.

Among the products obtained, $C_2$–$C_4$ light olefins, as well as benzene, toluene, ethylbenzene and xylenes have the highest commercial values and since enormous quantities are processes throughout the world, even small yield improvements lead to substantial profit increases.

In recent years, ZSM-5 zeolite catalysts have drawn considerable attention because of their ability to increase selectivity in a variety of industrial processes such as xylene isomerization, toluene disproportionation, aromatic alkylation and methanol conversion.

It has been shown that the zeolite's selectivity properties are the result of its tridimensional channel network and of the different pore sizes of its structure.

One of the most interesting areas where ZSM-5 zeolites have shown substantial catalytic activity is in the process in which methanol is converted into hydrocarbons. Thus, by using appropriate reaction conditions, very high yields in $C_5$–$C_{11}$ gasoline hydrocarbons can be obtained. However, this reaction presents the drawback of producing small quantities of durene, an undesirable reaction product.

Furthermore, modifications of the catalyst can also lead to highly efficient production of light olefins resulting from methanol conversion.

Thus, it can be seen that modified zeolite catalysts have the possibilities to present very interesting properties for enhancing yields in petrochemical reactions.

Therefore, since steam-cracking is one of the most widespread petrochemical processes, it would be highly desirable to provide means for increasing production of the most valuable reaction products.

SUMMARY OF THE INVENTION

The present invention relates to a process for up-grading products resulting from the steam-cracking of hydrocarbons which comprises bringing the steam-cracking reaction products in contact with a multifunctional Zn-ZSM-5 zeolite/$Cr_2O_3$/$Al_2O_3$ catalyst comprising of a mixture of from 2.5 to 7.5% wt of $Cr_2O_3$, 5 to 17.5% wt of $Al_2O_3$ and 75 to 85% wt of a Zn-ZSM-5 zeolite or a Zn-ZSM-5 zeolite/asbestos. Such a process allows for significant yield increases in $C_2$–$C_4$ olefins. Furthermore, the commonly obtained pyrolysis oil is up-graded to a high grade gasoline, rich in monoaromatics and free from undesirable durenes and long aliphatic chains.

DETAILED DESCRIPTION OF THE INVENTION

The main feature of the present invention resides in the presence of a catalytic reactor at the outlet of the steam-cracking reactor. This catalytic reactor contains a multifunctional catalyst which comprises a zeolite of the ZSM-5 type coupled with metallic oxides.

These oxides can either be coupled to the zeolite by being directly deposited on the zeolite or mechanically mixed with the zeolite.

The metallic oxides can be selected from oxides such as $Cr_2O_3$, $Al_2O_3$, or from any metallic oxide having a hydrogenating/dehydrogenating function.

In the case of the $Cr_2O_3$, $Al_2O_3$ proportions of $Cr_2O_3$ ranging between 2.5 and 7.5% wt, proportions of $Al_2O_3$ ranging between 5 and 17.5% wt and proportions of the zeolite catalyst ranging between 75 and 85% wt can be used.

Although the catalytic reactor used in the present invention was a fixed-bed reactor, it will be understood that any suitable design commonly used for catalytic reactions could have been chosen.

In the drawings:

FIG. 1 represents a schematic drawing of the bench scale setting for the catalytic up-grading of products resulting from the steamcracking of hydrocarbons.

FIG. 2 represents a comparison between the amounts of $C_2$–$C_4$ olefins obtained by steam-cracking alone and by steam-cracking along with various zeolite catalysts.

FIG. 3 represents a comparison between the amounts of ethylene obtained by steam-cracking alone and by steam-cracking along with various zeolite catalysts.

Referring now to FIG. 1, the starting hydrocarbon material 2 is first mixed with a stripping gas 4. It is to be noted, however, that the use of a stripping gas is optional. In the context of the actual experiments, a stripping gas was used only for convenience.

The resulting mixture is then forwarded to a vaporizer-mixer 6, in which steam is injected by means of an infusion pump 8. The gaseous mixture thus obtained enters a steam-cracking tubular reactor 10 heated at a temperature ranging between 760° and 860° C. In a further step, products coming out of the steamcracking tubular reactor 10 are sent into a catalytic reactor 12 heated at a temperature ranging between 450° and 550° C. The resulting products are then cooled by a series of condensers 14 (water-cooling condensers and ice bath). Immediately following the cooling step, the liquid and gaseous phases are separated. The liquids are first collected in a liquid-collector cylinder 16 while the gases flow through the liquid-collector cylinder to be collected for on line analysis in a dynamic sampler cylinder 18 located at a higher position than the liquid collector cylinder.

The present invention will be more readily understood by referring to the following examples which are given to illustrate rather than limit the scope of the invention.

EXAMPLE 1

Propane is the starting hydrocarbon material on which the steam-cracking process was performed. It was introduced into the system at a flow rate of 45 ml/min. or 4.95 g/hour. It was first mixed with helium acting as a stripping gas. After having been flown through the vaporizer-mixer, in which steam was injected at a rate of 1.7 g/hour, the gaseous mixture was then sent into the steam-cracking reactor whose internal temperature had been set to 780° C. at atmospheric pressure. The residence time of the starting material in the steam-cracking reactor was approximately 1 second.

The resulting product was then separated into its liquid and the gaseous phases. The liquid fraction was analyzed by GC using a capillary column (length: 50 m, PONA ® type, fused silica coated with a crosslinked polymer). The gases were analyzed on line by gas chromatography. A column having a length of 3.5 m packed with Chromosorb ® P coated with 20% by weight of Squalane ® was used for the analysis. The GC used was a dual FID Hewlett-Packard Model 5790 equipped with a 3392A Model integrator. Results are shown in Table 1.

EXAMPLE 2

The same procedure as in Example 1 was repeated the only modification being the internal temperature of the steam-cracking reactor which was set at 800° C. Results are shown in Table 1.

EXAMPLE 3

The same procedure as in Example 1 was repeated the only modification being the internal temperature of the steam-cracking reactor which was set at 835° C. Results are shown in Table 5.

EXAMPLE 5

As in Example 1 propane was chosen as the starting hydrocarbon material. It was mixed with helium and flown through the vaporizer-mixer. The gaseous mixture was then forwarded through the steam-cracking reactor whose internal temperature had been set to 780° C. The resulting products were then sent to the catalytic reactor which had been previously embedded with 4 g of a Zn-Mn-ZSM-5 zeolite which was prepared according to the procedure described in Can. patent application Ser. No. 471,463. The temperature of the catalytic reactor had been previously set at 500° C., with a pressure of 1 atmosphere and a W.H.S.V. (weight hourly space velocity) of 1 h$^{-1}$. The final products were analyzed using the techniques discussed in Example 1. Results are shown in Table 2.

EXAMPLE 5

The same procedure as in Example 4 was repeated, the only modification being the internal temperature of the steam-cracking reactor which was set at 800° C. Results are shown in Table 2.

EXAMPLE 6

The same procedure as in Example 4 was repeated, except for the following modifications: the catalytic reactor was embedded with 4 g of a Zn-Mn-ZSM-5 zeolite/asbestos catalyst prepared according to the procedure described in Can. patent application Ser. No. 471,463. Results are shown in Table 3.

EXAMPLE 7

The same procedure as in Example 6 was repeated, the only modification being the internal temperature of the steam-cracking reactor which was set at 800° C. Results are shown in Table 3.

EXAMPLE 8

The same procedure as in Example 4 was repeated, except for the following modification: the catalytic reactor was embedded with a Zn-ZSM-5 zeolite/asbestos/Cr$_2$O$_3$/Al$_2$O$_3$ catalyst. The Zn-ZSM-5 zeolite/asbestos catalyst was prepared according to the method described in Can. patent application Ser. No. 471,463 or related Le Van Mao U.S. Pat. No. 4,615,995. Then, 4.5 g of the Zn-ZSM-5 zeolite/asbestos catalyst obtained were wet with a solution prepared from 0.3 g of Cr$_2$O$_3$ and 0.4 g of sodium aluminate dissolved in 5 ml of distilled water. The resulting multifunctional catalyst was dried at 120° C. for 12 hours and actuated at 500° C. for another 12 hour period. Finally, the catalyst was reduced in hydrogen at 350° C. for at least 1 hour. Results are shown in Table 4.

EXAMPLE 9

The same procedure as in Example 8 was repeated, the only modification being the internal temperature of the steam-cracking reactor which was set at 800° C. Results were shown in Table 4.

When studying the results obtained from the various examples, it is to be noted that in the steamcracking process alone (Table 1) significant increases in highly valuable compounds such as ethylene, benzene and toluene are observed when the internal temperature of the reactor is increased from 780° to 800° C. The amount of less valuable products such as methane is higher at 800° C. but this increase is compensated by a decrease in C$_2$-C$_4$ paraffins.

As for the aromatic content, there is a dramatic decrease in less valuable C$_5$-C$_{11}$ aliphatics, resulting in the obtention of more interesting products such as benzene, xylenes and toluene. In examples 4 to 7, Zn-Mn-ZSM-5 zeolite and Zn-Mn-ZSM-5 zeolite/asbestos, two known catalysts were used to form the catalytic bed. As it can be seen in Tables 2 and 3, and in FIGS. 2 and 3, inferior results were obtained when compared to steam-cracking alone as far as the olefin content is concerned, regardless of the temperature at which the reactions were performed.

As for the aromatic content, better results were obtained, but these results are at the best sufficient and no more, to compensate the quality loss on the side of the olefin production, especially, as far as ethylene is concerned, since ethylene is the most valuable steam-cracking product.

Thus, in the light of these results, one could tend to be led away from using zeolite catalysts as means to improve steam-cracking processes.

In Examples 8 and 9, the results obtained by using a multifunctional catalyst point out better results in both olefin and aromatic productions. Thus, it has been discovered as it can be seen in FIGS. 2 and 3, that the use of metal oxides co-catalyst coupled with a zeolite type catalyst unexpectedly increases the amounts of valuable steam-cracking products. In fact, the total amount of C$_2$-C$_4$ olefins and especially ethylene obtained by using the multifunctional catalyst after a steam-cracking reaction of 780° (55.8% wt) is even superior to the amount obtained when performing the steam-cracking reaction alone at 800° (47.1 wt).

Moreover as described in Example 3, a run without catalyst was performed at 835° C. This temperature was fairly close to temperatures used in industrial steam-cracking facilities using propane as a starting hydrocarbon material. When the product distribution of such a run is compared to the run performed in presence of the Zn-ZSM-5 zeolite/asbestos/$Cr_2O_3$/$Al_2O_3$ catalyst and with the steam-cracking reactor temperature set at 800° C., as described in Example 9, it can be seen, as it is shown in Table 5, that in the presence of the multifunctional catalyst and with a much lower steam-cracking temperature, higher yields in ethylene and propylene were obtained. The propylene yield was nearly doubled (due mainly to a lower steam-cracking temperature) and the ethylene yield was increased by 5 wt percentage points while methane formation was significantly lower.

Furthermore, the liquid yield was much lower for the run performed at a lower steam-cracking temperature in the presence of the multifunctional catalyst. However, the BTX aromatics (benzene, toluene, ethylbenzene and xylenes) content in the liquid hydrocarbon products was much higher and there was no formation of undesirable hydrocarbons.

Thus, by performing the steam-cracking of propane at a lower temperature and using a multifunctional catalyst, the total "ethylene+propylene" yield can be increased by 10 wt percentage points and the ethylene/propylene wt ratio can be decreased to a very large extent (see Table 5).

From an industrial viewpoint, this would represent a real advantage since the present market trends are for a lower demand in ethylene and an increasing demand in propylene.

It will be appreciated that even though yields increase in valuable products ranging from 5 to 10% wt do not seem to be of significant importance, because of the enormous amounts of hydrocarbon material refined every day throughout the world, even a 0.5% wt yield increase represents millions of dollars of profits for petrochemical industries. Therefore, it is submitted that every invention increasing production yields in the petrochemical conversion processes has tremendous commercial values for these industries.

It will also be understood that although the process of the present invention has been developed for up-grading steam products, it can also be applied to every situation where starting materials such as pyrolysis oil, pyrolysis gasoline, mixtures of light olefins, light paraffins or mixture thereof are flown directly into the catalytic reactor without requiring any passage through a steam-cracking reactor.

In such cases, the multifunctional properties of the catalyst are expressed through several actions such as acid-catalyzed reactions (cracking, oligomerization, isomerization, transmutation) and redox reactions on intermediates leading to the final products or on the products themselves.

Therefore, in the framework of the present invention, the reactor containing the multifunctional catalyst can be located either after the steam-cracking reactor or after the liquid/gases separation operation (thus intercepting the liquid or gaseous products) and still obtain similar end results.

TABLE 1

DISTRIBUTION OF STEAM-CRACKING PRODUCTS OBTAINED IN THE ABSENCE OF CATALYST

| Gaseous Products | Commercial Value | Reaction Temperature °C. | | Liquid Products | Commercial Value | Reaction Temperature °C. | |
|---|---|---|---|---|---|---|---|
| | | 780% wt Obtained | 800% wt Obtained | | | 780% wt Obtained | 800% wt Obtained |
| | | | | LIQUID YEILD (wt %) | | 2.2[1] | 2.9[1] |
| ETHYLENE | Highest | 31.9 | 37.5 | BENZENE | Highest | 0.0 | 0.4 |
| PROPYLENE | ↓ | 11.8 | 10.9 | XYLENES | ↓ | 0.0 | 0.1 |
| (BUTENES + BUTADIENE) | ↓ | 3.4 | 3.5 | ETHYL-BENZENE | ↓ | 0.0 | 0.0 |
| ($C_2$ + $C_4$ PARAFFINS) | ↓ | 16.3 | 11.6 | TOLUENE | ↓ | 0.0 | 0.2 |
| PROPANE | ↓ | 16.7 | 10.7 | $C_9$-$C_{10}$ | ↓ | 0.0 | 0.5 |
| METHANE | Lowest | 17.7 | 22.9 | AROMATICS | ↓ | | |
| TOTAL OLEFIN YEILD (wt %) | | 47.1 | 51.9 | $C_5$-$C_{11}$ ALIPHATICS | Lowest | 2.2 | 1.7 |
| PROPANE CONVERSION (wt %) | | 83.3 | 89.3 | | | | |
| | | | | TOTAL AROMATIC CONTENT (%) | | 0.0 | 42 |

[1]Presence of hydrocarbons heavier than $C_{11}$

TABLE 2

COMPARISON OF DISTRIBUTION OF STEAM-CRACKING PRODUCTS OBTAINED IN THE ABSENCE OF CATALYST AND IN THE PRESENCE OF Zn—Mn—ZSM-5 ZEOLITE CATALYST

| Gaseous Products | Commercial Value | Steam-Cracking Temperature (°C.) | | | |
|---|---|---|---|---|---|
| | | 780% wt obtained no catalyst | 780% wt obtained Zn—Mn—ZSM-5 catalyst | 800% wt obtained no catalyst | 800% wt obtained Zn—Mn—ZSM-5 catalyst |
| ETHYLENE | Highest | 31.9 | 22.9 | 37.5 | 32.8 |
| PROPYLENE | ↓ | 11.8 | 12.1 | 10.9 | 10.7 |
| (BUTENES + BUTADIENE) | ↓ | 3.4 | 8.7 | 3.5 | 6.3 |
| ($C_2$ +$C_4$ PARAFFINS) | ↓ | 16.3 | 15.2 | 11.6 | 10.4 |
| PROPANE | ↓ | 16.7 | 14.4 | 10.7 | 8.6 |
| METHANE | Lowest | 17.7 | 19.7 | 22.9 | 24.4 |
| PROPANE CONVERSION (wt %) | | 83.3 | 85.6 | 89.3 | 91.4 |
| TOTAL OLEFIN YIELD (wt %) | | 47.1 | 43.7 | 51.9 | 49.8 |

TABLE 2-continued
COMPARISON OF DISTRIBUTION OF STEAM-CRACKING PRODUCTS OBTAINED IN THE ABSENCE OF CATALYST AND IN THE PRESENCE OF Zn—Mn—ZSM-5 ZEOLITE CATALYST

| Liquid Products | Commercial Value | Stream-Cracking Temperature (°C.) | | | |
|---|---|---|---|---|---|
| | | 780% wt obtained no catalyst | 780% wt obtained Zn—Mn—ZSM-5 catalyst | 800% wt obtained no catalyst | 800% wt obtained Zn—Mn—ZSM-5 catalyst |
| LIQUID YIELD (wt %) | | 2.2[1] | 7.1[2] | 2.9[1] | 6.8[2] |
| BENZENE | Highest | 0.0 | 0.7 | 0.4 | 0.7 |
| XYLENES | ↓ | 0.0 | 0.9 | 0.1 | 0.8 |
| ETHYL-BENZENE | ↓ | 0.0 | 0.4 | 0.0 | 0.5 |
| TOLUENE | ↓ | 0.0 | 1.0 | 0.2 | 1.2 |
| $C_9$–$C_{10}$ AROMATICS | ↓ | 0.0 | 1.1 | 0.5 | 0.9 |
| $C_5$–$C_{11}$ ALIPHATICS | Lowest | 2.2 | 3.0 | 1.7 | 2.7 |
| TOTAL AROMATIC Content (%) | | 0.0 | 58 | 42 | 61 |

[1] Presence of hydrocarbons heavier than $C_{11}$
[1] Absence of hydrocarbons heavier than $C_{11}$

TABLE 3
COMPARISON OF DISTRIBUTION OF STEAM-CRACKING PRODUCTS OBTAINED IN THE ABSENCE OF CATALYST AND IN THE PRESENCE OF Zn—Mn—ZSM-5 ZEOLITE/ASBESTOS CATALYST

| Gaseous Products | Commercial Value | Steam-Cracking Temperature (°C.) | | | |
|---|---|---|---|---|---|
| | | 780% wt obtained no catalyst | 780% wt obtained Zn—Mn—ZSM-5 zeolite/asbestos catalyst | 800% wt obtained no catalyst | 800% wt obtained Zn—Mn—ZSM-5 zeolite/asbestos catalyst |
| ETHYLENE | Highest | 31.9 | 22.7 | 37.5 | 31.5 |
| PROPYLENE | ↓ | 11.8 | 11.6 | 10.9 | 11.3 |
| (BUTENES + BUTADIENE) | ↓ | 3.4 | 8.4 | 3.5 | 8.2 |
| ($C_2$ + $C_4$ PARAFFINS) | ↓ | 16.3 | 16.5 | 11.6 | 10.3 |
| PROPANE | ↓ | 16.7 | 16.8 | 10.7 | 8.3 |
| METHANE | Lowest | 17.7 | 18.4 | 22.9 | 23.8 |
| PROPANE CONVERSION (wt %) | | 83.3 | 83.2 | 89.3 | 91.7 |
| TOTAL OLEFIN YIELD (wt %) | | 47.1 | 42.7 | 51.9 | 51.0 |

| Liquid Products | Commercial Value | Steam-Cracking Temperature (°C.) | | | |
|---|---|---|---|---|---|
| | | 780% wt obtained no catalyst | 780% wt obtained Zn—Mn—ZSM-5 zeolite/asbestos | 800% wt obtained no catalyst | 800% wt obtained Zn—Mn—ZSM-5 zeolite/asbestos catalyst |
| LIQUID YIELD (wt %) | | 2.2[1] | 5.7[2] | 2.9[1] | 6.7[2] |
| BENZENE | Highest | 0.0 | 0.4 | 0.4 | 0.4 |
| XYLENES | ↓ | 0.0 | 0.5 | 0.1 | 0.7 |
| ETHYL-BENZENE | ↓ | 0.0 | 0.4 | 0.0 | 0.4 |
| TOLUENE | ↓ | 0.0 | 0.9 | 0.2 | 1.2 |
| $C_9$–$C_{10}$ AROMATICS | ↓ | 0.0 | 1.0 | 0.5 | 1.2 |
| $C_5$–$C_{11}$ ALIPH. | Lowest | 2.2 | 2.5 | 1.7 | 2.8 |
| TOTAL AROMATIC CONTENT (%) | | 0.0 | 56 | 42 | 58 |

[1] Presence of hydrocarbons heavier than $C_{11}$
[2] Absence of hydrocarbons heavier than $C_{11}$

TABLE 4
COMPARISON OF DISTRIBUTION OF STEAM-CRACKING PRODUCTS OBTAINED IN THE ABSENCE OF CATALYST AND IN THE PRESENCE OF Zn—ZSM-5 ZEOLITE/ASBESTOS/$Cr_2O_3$/$Al_2O_3$ CATALYST

| | Steam-Cracking Temperature (°C.) | |
|---|---|---|
| | 780% wt | 800% wt |

TABLE 4-continued
COMPARISON OF DISTRIBUTION OF STEAM-CRACKING PRODUCTS OBTAINED IN THE ABSENCE OF CATALYST AND IN THE PRESENCE OF Zn—ZSM-5 ZEOLITE/ASBESTOS/$Cr_2O_3$/$Al_2O_3$ CATALYST

| Gaseous Products | Commercial Value | 780% wt obtained no catalyst | 780% wt obtained Zn—ZSM-5 zeolite/ asbestos/ $Cr_2O_3$/$Al_2O_3$ Catalyst | 800% wt obtained no catalyst | 800% wt obtained Zn—ZSM-5 zeolite/ asbestos/ $Cr_2O_3$/$Al_2O_3$ Catalyst |
|---|---|---|---|---|---|
| ETHYLENE | Highest | 31.9 | 41.5 | 37.5 | 46.2 |
| PROPYLENE | ↓ | 11.8 | 11.4 | 10.9 | 8.7 |
| (BUTENES + BUTADIENE) | ↓ | 3.4 | 2.9 | 3.5 | 3.2 |
| ($C_2$ + $C_4$ PARRAFINS) | ↓ | 16.3 | 10.5 | 11.6 | 6.9 |
| PROPANE | ↓ | 16.7 | 8.2 | 10.7 | 4.0 |
| METHANE | Lowest | 17.7 | 23.4 | 22.9 | 27.9 |
| PROPANE CONVERSION (wt %) | | 83.3 | 91.8 | 89.3 | 96.0 |
| TOTAL OLEFIN YIELD (wt %) | | 47.1 | 55.8 | 51.9 | 58.1 |

| Liquid Products | Commercial Value | 780% wt obtained no catalyst | 780% wt obtained Zn—ZSM-5 zeolite/ asbestos/ $Cr_2O_3$/$Al_2O_3$ Catalyst | 800% wt obtained no catalyst | 800% wt obtained Zn—ZSM-5 zeolite/ asbestos/ $Cr_2O_3$/$Al_2O_3$ Catalyst |
|---|---|---|---|---|---|
| LIQUID YIELD (wt %) | | 2.2[1] | 2.1[2] | 2.9[1] | 3.1[2] |
| BENZENE | Highest | 0.0 | 0.2 | 0.4 | 0.4 |
| XYLENES | ↓ | 0.0 | 0.2 | 0.1 | 0.4 |
| ETHYL-BENZENE | ↓ | 0.0 | 0.1 | 0.0 | 0.3 |
| TOLUENE | ↓ | 0.0 | 0.2 | 0.2 | 0.7 |
| $C_9$-$C_{10}$ AROMATICS | ↓ | 0.0 | 0.6 | 0.5 | 0.5 |
| $C_5$-$C_{11}$ ALIPH. | Lowest | 2.2 | 0.8 | 1.7 | 0.8 |
| TOTAL AROMATIC CONTENT (%) | | 0.0 | 57 | 42 | 73 |

[1] Presence of hydrocarbons heavier than $C_{11}$
[2] Absence of hydrocarbons heavier than $C_{11}$

TABLE 5
COMPARISON OF DISTRIBUTION OF STEAM-CRACKING PRODUCTS OBTAINED IN THE ABSENCE OF CATALYST AT 835° C. AND IN THE PRESENCE OF Zn—ZSM-5 ZEOLITE/ASBESTOS/$Cr_2O_3$/$Al_2O_3$ CATALYST AT 800° C.

| Gaseous Products | Commercial Value | Steam-Cracking Temperature (°C.) 835% wt obtained no catalyst | Steam-Cracking Temperature (°C.) 800% wt obtained Zn—ZSM-5 zeolite/asbestos/ $Cr_2O_3$/$Al_2O_3$ catalyst | Liquid Products | Steam-Cracking Temperature (°C.) 835% wt obtained no catalyst | Steam-Cracking Temperature (°C.) 800% wt obtained Zn—ZSM-5 zeolite/asbestos/ $Cr_2O_3$/$Al_2O_3$ catalyst |
|---|---|---|---|---|---|---|
| ETHYLENE | Highest | 41.2 | 46.2 | LIQUID HYDROCARBON YIELD (wt %) | 7.8 | 3.1 |
| PROPYLENE | ↓ | 4.5 | 8.7 | Total aromatic content (%) | 78.4 | 73.1 |
| (BUTENES + BUTADIENE) | ↓ | 3.2 | 3.2 | | | |
| ($C_2$ + $C_4$ PARAFFINS) | ↓ | 7.7 | 6.9 | BTX aromatic content (%) | 48.3 | 58.2 |
| PROPANE | ↓ | 6.1 | 4.0 | Liquid hydrocarbons heavier than $C_{11}$ (%) | 4.0 | 0.0 |
| METHANE | Lowest | 29.5 | 27.9 | | | |
| PROPANE CONVERSION (wt %) | | 93.9 | 96.0 | | | |
| (ETHYLENE + PROPYLENE) YIELD (wt %) | | 45.7 | 54.9 | | | |
| ETHYLENE/PROPYLENE wt ratio | | 9.2 | 5.3 | | | |

What is claimed is:

1. A catalyst suitable for up-grading products resulting from the steam-cracking of hydrocarbons, said catalyst comprising 2.5 to 7.5% wt of $Cr_2O_3$, 5 to 17.5% wt of $Al_2O_3$ and 75 to 85% wt of a Zn-ZSM-5 zeolite or a Zn-ZSM-5 zeolite/asbestos.

2. The catalyst of claim 1, wherein $CR_2O_3$ and $Al_2O_3$ are mechanically mixed with the Zn-ZSM-5 zeolite or the Zn-ZSM-5 zeolite/asbestos.

3. The catalyst of claim 1, wherein $Cr_2O_3$ and $Al_2O_3$ are directly deposited on the Zn-ZSM-5 zeolite or the Zn-ZSM-5 zeolite/asbestos.

4. A catalyst according to claim 1 consisting of 2.5 to 7.5% wt. of $Cr_2O_3$, 5 to 17.5% st. of $Al_2O_3$ and 75 to 85% wt. of an Zn-ZSM-5 zeolite or Zn-ZSM-5 zeolite asbestos.

5. The catalyst according to claim 4 wherein $CR_2O_3$ and $Al_2O_3$ are mechanically mixed with the Zn-ZSM-5 zeolite or the Zn-ZSM-5 zeolite/asbestos.

6. The catalyst according to claim 4 wherein $CR_2O_3$ and $Al_2O_3$ are directly deposited on the Zn-ZSM-5 zeolite or the Zn-ZSM-5 zeolite/asbestos.

* * * * *